United States Patent
Shin et al.

(10) Patent No.: US 11,753,665 B2
(45) Date of Patent: Sep. 12, 2023

(54) METHOD FOR IMPROVING PRODUCTIVITY OF 2'-FUCOSYLLACTOSE THROUGH ENZYMATIC TREATMENT

(71) Applicants: Advanced Protein Technologies Corp., Suwon-si (KR); SEOUL NATIONAL UNIVERSITY R&DB FOUNDATION, Seoul (KR)

(72) Inventors: Chui Soo Shin, Suwon-si (KR); Jong Won Yoon, Seongnam-si (KR); Young Ha Song, Yongin-si (KR); Jong Gil Yoo, Suwon-si (KR); Young Sun Yoo, Hwaseong-si (KR); Heon Hak Lee, Pyeongtaek-si (KR)

(73) Assignees: Advanced Protein Technologies Corp., Suwon-si (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 18/000,246

(22) PCT Filed: Nov. 1, 2022

(86) PCT No.: PCT/KR2022/016912
§ 371 (c)(1),
(2) Date: Nov. 29, 2022

(65) Prior Publication Data
US 2023/0193334 A1    Jun. 22, 2023

(30) Foreign Application Priority Data

Nov. 24, 2021 (KR) .................. 10-2021-0163686

(51) Int. Cl.
| | | |
|---|---|---|
| C12P 19/04 | (2006.01) | |
| C12N 9/90 | (2006.01) | |
| C12N 9/88 | (2006.01) | |
| C12N 9/02 | (2006.01) | |
| C12N 9/26 | (2006.01) | |
| C12N 9/04 | (2006.01) | |
| C12N 9/12 | (2006.01) | |
| C12N 15/77 | (2006.01) | |
| C12P 19/00 | (2006.01) | |
| C12N 9/24 | (2006.01) | |
| C12N 9/10 | (2006.01) | |

(52) U.S. Cl.
CPC ............ *C12P 19/00* (2013.01); *C12N 9/1051* (2013.01); *C12N 9/2402* (2013.01); *C12Y 204/01069* (2013.01); *C12Y 302/01023* (2013.01)

(58) Field of Classification Search
CPC ....... C12P 19/04; C12N 9/051; C12N 9/2408; C12N 9/0006; C12N 9/88; C12N 15/77; C12N 9/1205; C12N 9/90; C12N 9/1241; C12Y 204/01069; C12Y 302/01023
See application file for complete search history.

(56) References Cited

U.S. PATENT DOCUMENTS 10,570,399 B2 *   2/2020   Seo .................. C07K 14/34
2020/0048640 A1   2/2020   Seo et al.

FOREIGN PATENT DOCUMENTS

| EP | 3 450 562 A1 | 3/2019 |
|---|---|---|
| KR | 2002-0062361 A | 7/2002 |
| KR | 10-1544184 B1 | 8/2015 |
| KR | 10-1648352 B1 | 8/2016 |
| KR | 10-1731263 B1 | 5/2017 |
| KR | 10-2014925 B1 | 8/2019 |
| KR | 10-2021-0028292 A | 3/2021 |
| WO | 2017/188684 A1 | 11/2017 |

OTHER PUBLICATIONS

Young-Wook Chin et al., "Metabolic engineering of *Corynebacterium glutamicum* to produce GDP-L-fucose from glucose and mannose", Bioprocess Biosyst Eng, 2013, vol. 36, pp. 749-756 (8 pages total).
International Search Report dated Feb. 3, 2023 issued by the International Searching Authority in Application No. PCT/KR2022/016912.
Notification of Opinion Submission of KR-10-2021-0163686 dated Jan. 6, 2022.
Notification of Opinion Submission of KR-10-2021-0163686 dated May 27, 2022.

* cited by examiner

*Primary Examiner* — Maryam Monshipouri
(74) *Attorney, Agent, or Firm* — Sughrue Mion, PLLC

(57) ABSTRACT

Disclosed is a method for improving the productivity of 2'-fucosyllactose (2'-FL) through enzymatic treatment. Lactose used as a substrate in the stationary phase during culture is degraded by treatment with a small amount of enzyme, the resulting glucose is consumed to produce guanosine diphosphate-L-fucose as a precursor of 2'-fucosyllactose, and the use of lactose left after culture can be maximally utilized for the production of 2'-fucosyllactose. As a result, it is possible to increase the productivity of 2'-fucosyllactose in an economically efficient manner because additional glucose is not required while minimizing by-products.

5 Claims, 3 Drawing Sheets

Specification includes a Sequence Listing.

| Time(hr) | DCW | 2'-FL | Lactose | Glucose | Etc |
|---|---|---|---|---|---|
| 0 | 0.00 | 0.00 | 19.70 | 40.10 | |
| 23 | 27.18 | 2.30 | 19.10 | 0.30 | |
| 48 | 78.72 | 16.60 | 29.60 | 0.30 | |
| 72 | 70.32 | 30.10 | 32.20 | 6.20 | Feed of lactase |
| 78 | 79.32 | 33.70 | 21.00 | 4.90 | |
| 96 | 45.36 | 38.10 | 1.80 | 6.40 | |

SEQUENCE LISTING

```
Sequence total quantity: 19
SEQ ID NO: 1            moltype = DNA  length = 1122
FEATURE                 Location/Qualifiers
source                  1..1122
                        mol_type = genomic DNA
                        organism = Escherichia coli
SEQUENCE: 1
atgtcaaaag tcgctctcat caccggtgta accggacaag acggttctta cctggcagag   60
tttctgctgg aaaaaggtta cgaggtgcat ggtattaagc gtcgcgcatc gtcattcaac  120
accgagcgcg tggatcacat ttatcaggat ccgcacacct gcaacccgaa attccatctg  180
cattatggcg acctgagtga tacctctaac ctgacgcgca ttttgcgtga agtacagccg  240
gatgaagtgt acaacctggg cgcaatgagc cacgttgcgg tctcttttga gtcaccagaa  300
tataccgctg acgtcgacgc gatgggtacg ctgcgcctgc tggaggcgat ccgcttcctc  360
ggtctggaaa agaaaactcg tttctatcag gcttccacct ctgaactgta tggtctggtg  420
caggaaattc cgcagaaaga gaccacgccg ttctacccgc gatctccgta tgcggtcgcc  480
aaactgtacg cctactggat caccgttaac taccgtgaat cctacggcat gtacgcctgt  540
aacggaattc tcttcaacca tgaatcccgc cgccgcgcg aaaccttcgt tacccgcaaa  600
atcacccgcg caatcgccaa catcgcccag gggctggagt cgtgcctgta cctcggcaat  660
atggattccc tgcgtgactg gggccacgcc aaagactacg taaaaatgca gtggatgatg  720
ctgcagcagg aacagccgga agatttcgtt atcgcgaccg gcgttcagta ctccgtgcgt  780
cagttcgtgg aaatggcggc agcacagctg ggcatcaaac tgcgctttga aggcacgggc  840
gttgaagaga agggcattgt ggtttccgtc accgggcatg acgcgccggg cgttaaaccg  900
ggtgatgtga ttatcgctgt tgaccgcgt tacttccgtc cggctgaagt tgaaacgctg  960
ctcggcgacc cgaccaaagc gcacgaaaaa ctgggctgga aaccggaaat cacccctcaga 1020
gagatggtgt ctgaaatggt ggctaatgac ctcgaagcgg cgaaaaaaca ctctctgctg 1080
aaatctcacg gctacgacgt ggcgatcgcg ctggagtcat aa                    1122

SEQ ID NO: 2            moltype = DNA  length = 966
FEATURE                 Location/Qualifiers
source                  1..966
                        mol_type = genomic DNA
                        organism = Escherichia coli
SEQUENCE: 2
atgagtaaac aacgagtttt tattgctggt catcgcggga tggtcggttc cgccatcagg   60
cggcagctcg aacagcgcgg tgatgtggaa ctggtattac gcacccgcga cgagctgaac  120
ctgctggaca gccgcgccgt gcatgatttc tttgccagcg aacgtattga ccaggtctat  180
ctggcggcgg cgaaagtggg cggcattgtt gccaacaaca cctatccggc ggatttcatc  240
taccagaaca tgatgattga gagcaacatc attcacgccg cgcatcagaa cgacgtgaac  300
aaactgctgt ttctcggatc gtcctgcatc taccgaaac tggcaaaaca gccgatggca  360
gaaagcgagt tgttgcaggg cacgctggag ccgactaacg agccttatgc tattgccaaa  420
atcgccggga tcaaactgtg cgaatcatac aaccgccagt acggacgcga ttaccgctca  480
gtcatgccga ccaacctgta cgggccacac gacaacttcc acccgagtaa ttcgcatgtg  540
atcccagcat tgctgcgtcg cttccacgag gcgacggcac agaatgcgcc ggacgtggtg  600
gtatgggca gcggtacacc gatgcgcgaa tttctgcacg tcgatgatat ggcggcggcg  660
agcattcatg tcatggagct ggcgcatgaa gtctggctgg agaacaccca gccgatgttg  720
tcgcacatta acgtcggcac gggcgttgac tgcactatcc gcgagctggc gcaaaccatc  780
gccaaagtgg tgggttacaa aggccgggtg gttttttgatg ccagcaaacc ggatggcacg  840
ccgcgcaaac tgctggatgt gacgcgcctg catcagcttg gctggtatca cgaaatctca  900
ctggaagcgg ggcttgccag cacttaccag tggttccttg agaatcaaga ccgctttcgg  960
gggtaa                                                             966

SEQ ID NO: 3            moltype = DNA  length = 1254
FEATURE                 Location/Qualifiers
source                  1..1254
                        mol_type = genomic DNA
                        organism = Escherichia coli
SEQUENCE: 3
atgtactatt taaaaaacac aaactttgg atgttcggtt tattctttt cttttacttt   60
tttatcatgg gagcctactt cccgttttc ccgatttggc tacatgacat caaccatatc  120
agcaaaagtg atacgggtat tattttgcc gctatttctc tgttctcgct attattccaa  180
ccgctgtttg gtctgctttc tgacaaactc gggctgcgca aatacctgct gtggattatt  240
```

```
accggcatgt tagtgatgtt tgcgccgttc tttattttta tcttcgggcc actgttacaa    300
tacaacattt tagtaggatc gattgttggt ggtatttatc taggcttttg ttttaacgcc    360
ggtgcgccag cagtagaggc atttattgag aaagtcagcc gtcgcagtaa tttcgaattt    420
ggtcgcgcgc ggatgtttgg ctgtgttggc tgggcgctgt gtgcctcgat tgtcggcatc    480
atgttcacca tcaataatca gtttgttttc tggctgggct ctggctgtgc actcatcctc    540
gccgttttac tcttttttcgc caaaacggat gcgcccctct ctgccacggt tgcaatgcg    600
gtaggtgcca accattcggc atttagcctt aagctggcac tggaactgtt cagacagcca    660
aaactgtggt ttttgtcact gtatgttatt ggcgtttcct gcacctacga tgttttttgac   720
caacagtttg ctaatttctt tacttcgttc tttgctaccg gtaacaggg tacgcgggta    780
tttggctacg taacgacaat gggcgaatta cttaacgcct cgattatgtt ctttgcgcca    840
ctgatcatta atcgcatcgg tgggaaaaac gccctgctgc tggctggcac tattatgtct    900
gtacgtatta ttggctcatc gttcgccacc tcagcgctga agtggttat tctgaaaacg    960
ctgcatatgt ttgaagtacc gttcctgctg gtgggctgct ttaaatatat taccagccag   1020
tttgaagtgc gttttcagc gacgatttat ctggtctgtt tctgcttctt taagcaactg   1080
gcgatgattt ttatgtctgt actggcgggc aatatgtatg aaagcatcgg tttccagggc   1140
gcttatctgg tgctgggtct ggtggcgctg ggcttcacct taatttccgt gttcacgctt   1200
agcggccccg gcccgctttc cctgctgcgt cgtcaggtga atgaagtcgc ttaa         1254

SEQ ID NO: 4              moltype = DNA   length = 807
FEATURE                   Location/Qualifiers
source                    1..807
                          mol_type = genomic DNA
                          organism = unidentified
SEQUENCE: 4
atgatatttg taaccggata tggccagatg tgtaacaaca tccttcaatt tgggcatttc     60
tttgcttatg caaaaagaaa tggtttaaaa acgttggct tacgttttg ctacaaatac    120
acttttttca agattagtaa cgaaaaaggc tataattggc cgacctatct ttatgcaaaa    180
tatgggcaa aaataggact tataaagtct gttgattttg acgaatcatt cgaaggtaca    240
aatgtagatt ctcttcaatt agacaaacaa accgtgttag ccaaaggctg gtattttaga    300
gactaccagg gatttcttaa ttaccgtaat gagcttaaag cactttttcga ctttaaagag   360
catattaaga aaccggtaga acagtttttt tcaacgttat caaagacac catcaaagta    420
ggcctgcata taagacgtgg tgattataag acctggcacc agggtaaata cttttttagc    480
gacgaagaat acggtcaaat cgtaaattct tttgctaaaa gtttagataa accggtagaa    540
ttaattattg ttagcaatga tcccaaacta aacagcaaaa gttttgaaaa tttaacatcc    600
tgtaaagtat caatgttaaa tggcaatcct gccgaagatc tttaccttct ttctaaatgt    660
gattatatta ttggccctcc cagcactttt tctttaatgg cagcttttta cgaagaccgc    720
cctttatatt ggatatttga taagaaaaaa cagcttttag cagaaaactt tgacaagttc    780
gagaatctgt ttcgacacat tatttaa                                        807

SEQ ID NO: 5              moltype = AA    length = 268
FEATURE                   Location/Qualifiers
source                    1..268
                          mol_type = protein
                          organism = unidentified
SEQUENCE: 5
MIFVTGYGQM CNNILQFGHF FAYAKRNGLK TVGLRFCYKY TFFKISNEKG YNWPTYLYAK     60
YGAKIGLIKS VDFDESFEGT NVDSLQLDKQ TVLAKGWYFR DYQGFLNYRN ELKALFDFKE    120
HIKKPVEQFF STLSKDTIKV GLHIRRGDYK TWHQGKYFFS DEEYGQIVNS FAKSLDKPVE    180
LIIVSNDPKL NSKSFENLTS CKVSMLNGNP AEDLYLLSKC DYIIGPPSTF SLMAAFYEDR    240
PLYWIFDKEK QLLAENFDKF ENLFRHII                                       268

SEQ ID NO: 6              moltype = DNA   length = 43
FEATURE                   Location/Qualifiers
source                    1..43
                          mol_type = other DNA
                          organism = synthetic construct
SEQUENCE: 6
gtcatatgat ggtcgcggat ccgaattccc aggcaagctc cgc                       43

SEQ ID NO: 7              moltype = DNA   length = 45
FEATURE                   Location/Qualifiers
source                    1..45
                          mol_type = other DNA
                          organism = synthetic construct
SEQUENCE: 7
gttttttaaa tagtacataa tctcgccttt cgtaaaaatt ttggt                     45

SEQ ID NO: 8              moltype = DNA   length = 55
FEATURE                   Location/Qualifiers
source                    1..55
                          mol_type = other DNA
                          organism = synthetic construct
SEQUENCE: 8
ttacgaaagg cgagattatg tactatttaa aaaacacaaa cttttggatg ttcgg          55
```

```
SEQ ID NO: 9              moltype = DNA  length = 58
FEATURE                   Location/Qualifiers
source                    1..58
                          mol_type = other DNA
                          organism = synthetic construct
SEQUENCE: 9
gcctttcgtt ttatttgctc gagtgcggcc gcttaagcga cttcattcac ctgacgac      58

SEQ ID NO: 10             moltype = DNA  length = 38
FEATURE                   Location/Qualifiers
source                    1..38
                          mol_type = other DNA
                          organism = synthetic construct
SEQUENCE: 10
tggagctcca ccgcggtggc tggccgttac cctgcgaa                            38

SEQ ID NO: 11             moltype = DNA  length = 31
FEATURE                   Location/Qualifiers
source                    1..31
                          mol_type = other DNA
                          organism = synthetic construct
SEQUENCE: 11
caaatatcat tgtatgtcct cctggacttc g                                   31

SEQ ID NO: 12             moltype = DNA  length = 32
FEATURE                   Location/Qualifiers
source                    1..32
                          mol_type = other DNA
                          organism = synthetic construct
SEQUENCE: 12
aggacataca atgatatttg taaccggata tg                                  32

SEQ ID NO: 13             moltype = DNA  length = 45
FEATURE                   Location/Qualifiers
source                    1..45
                          mol_type = other DNA
                          organism = synthetic construct
SEQUENCE: 13
cgcttcacta gttctagagc ttaaataatg tgtcgaaaca gattc                    45

SEQ ID NO: 14             moltype = DNA  length = 56
FEATURE                   Location/Qualifiers
source                    1..56
                          mol_type = other DNA
                          organism = synthetic construct
SEQUENCE: 14
ttggagctcc accgcggtgg cggccgctct agaactagtg aagcgcctca tcagcg        56

SEQ ID NO: 15             moltype = DNA  length = 60
FEATURE                   Location/Qualifiers
source                    1..60
                          mol_type = other DNA
                          organism = synthetic construct
SEQUENCE: 15
tacaccggtg atgagagcga cttttgacat ggtaaaaaat cctttcgtag gtttccgcac    60

SEQ ID NO: 16             moltype = DNA  length = 30
FEATURE                   Location/Qualifiers
source                    1..30
                          mol_type = other DNA
                          organism = synthetic construct
SEQUENCE: 16
atgtcaaaag tcgctctcat caccggtgta                                     30

SEQ ID NO: 17             moltype = DNA  length = 30
FEATURE                   Location/Qualifiers
source                    1..30
                          mol_type = other DNA
                          organism = synthetic construct
SEQUENCE: 17
caagctgaat tcttaccccc gaaagcggtc                                     30

SEQ ID NO: 18             moltype = DNA  length = 30
FEATURE                   Location/Qualifiers
source                    1..30
                          mol_type = other DNA
                          organism = synthetic construct
```

```
SEQUENCE: 18
gaccgctttc gggggtaaga attcagcttg                                        30

SEQ ID NO: 19           moltype = DNA  length = 60
FEATURE                 Location/Qualifiers
source                  1..60
                        mol_type = other DNA
                        organism = synthetic construct
SEQUENCE: 19
ggtatcgata agcttgatat cgaattcctg cagcccgggg aaaaggccat ccgtcaggat        60
```

METHOD FOR IMPROVING PRODUCTIVITY OF 2'-FUCOSYLLACTOSE THROUGH ENZYMATIC TREATMENT

CROSS REFERENCE TO RELATED APPLICATIONS

This application is a National Stage of International Application No. PCT/KR2022/016912 filed on Nov. 1, 2022, claiming priority based on Korean Patent Application No. 10-2021-0163686 filed on Nov. 24, 2021, the entire disclosures of which are incorporated herein by reference.

INCORPORATION BY REFERENCE OF SEQUENCE LISTING

The content of the electronically submitted sequence listing, file name: Q282686_sequence listing as filed.XML; size: 22,435; and date of creation: Nov. 28, 2022, filed herewith, is incorporated herein by reference in their entirety.

DESCRIPTION

Technical Field

The present invention relates to a method for improving the productivity of 2'-fucosyllactose (2'-FL) through enzymatic treatment, and more specifically, to a method for improving the productivity of 2'-fucosyllactose (2'-FL) through enzymatic treatment based on a lactose substrate, without using any additional medium.

Background Art

Human milk oligosaccharides (HMOs) are oligosaccharides contained in human milk, which are the third most abundant component after lactose and fat. There are about 200 types of a variety of human milk oligosaccharides. Human milk oligosaccharides have advantages of strengthening the immune function or having positive effects on the development and behaviors of children.

2'-fucosyllactose, which is present in the largest amount in major HMOs, is involved in various biological activities. Methods for preparing 2'-fucosyllactose reported by previous research include direct extraction from breast milk and extraction based on chemical or enzymatic treatment. However, direct extraction from breast milk has problems in that it is unethical, breast milk supply is limited and productivity is low. In addition, the chemical synthesis method has problems such as expensive substrates, low isomer selectivity and yield, the necessity of use of toxic reagents and high purification costs and the enzymatic synthesis method has problems in that GDP-L-fucose used as a precursor is very expensive and the purification cost of the fucose transferase is high.

In an approach to these problems, 2'-fucosyllactose may be prepared using microorganisms. However, most conventional methods of preparing 2'-fucosyllactose have used recombinant *E. coli*. However, it is recognized as a harmful germ by consumers and *E. coli* cells are limitedly used due to a phenomenon called "lactose killing" in which *E. coli* cells may be killed under lactose-restricted culture by lactose permease (Daniel Dykhuizen and Daniel Hartl, 1987, "Transport by the lactose permease of Escherichia coli as the basis of lactose killing", 10.1128/JB.135.3.876-882, 1978, Journal of Bacteriology). Accordingly, there is a need for a novel method for preparing 2-fucosyllactose to improve the productivity in a safe and economically efficient manner, while overcoming the drawbacks of conventional methods.

DISCLOSURE

Technical Problem

It is an object of the present invention to provide a method for improving the productivity of 2'-fucosyllactose (2'-FL) by degrading lactose as a substrate through enzymatic treatment in an economically efficient manner, without using any additional medium.

Technical Solution

In accordance with one aspect of the present invention, the above and other objects can be accomplished by the provision of a method for preparing 2'-fucosyllactose by culturing recombinant *Corynebacterium glutamicum* in a medium supplemented with lactose, wherein the recombinant *Corynebacterium glutamicum* is transformed to express α-1,2-fucosyltransferase, is transformed to express GDP-D-mannose-4,6-dehydratase, is transformed to express GDP-L-fucose synthase, and is transformed to express lactose permease, and the *Corynebacterium glutamicum* has phosphomannomutase and GTP-mannose-1-phosphate guanylyltransferase, wherein a lactase is fed to the medium in a stationary phase or death phase.

Meanwhile, preferably, the recombinant *Corynebacterium glutamicum* is transformed to overexpress phosphomannomutase, and is transformed to overexpress GTP-mannose-1-phosphate guanylyltransferase.

Meanwhile, the medium preferably contains glucose.

Meanwhile, the method is preferably performed by fed-batch culture of further feeding glucose or lactose during culture.

Meanwhile, the lactase is preferably fed to the medium at a time of transition from the stationary phase to the death phase.

Advantageous Effects

In the present invention, lactose used as a substrate in the stationary phase during culture is degraded by treatment with a small amount of enzyme, the resulting glucose is consumed to produce guanosine diphosphate-L-fucose as a precursor of 2'-fucosyllactose, and the use of lactose left after culture can be maximally utilized for the production of 2'-fucosyllactose. As a result, it is possible to increase the productivity of 2'-fucosyllactose in an economically efficient manner because additional glucose is not required while minimizing by-products.

Description of Drawings

The above and other objects, features, and other advantages of the present invention will be more clearly understood from the following detailed description taken in conjunction with the accompanying drawings, in which.

BEST MODE

2'-fucosyllactose, which is a main ingredient of human milk oligosaccharides, has health functional advantages such as being involved in various biological activities, and various methods for producing the same have been developed. However, direct extraction from breast milk and chemical or enzymatic synthesis have problems such as low productivity, high costs, low production yield, and toxicity. Therefore, there is a need for alternatives thereto.

As an alternative, preparation of 2'-fucosyllactose using microorganisms has been suggested. However, most conventional methods of preparing 2'-fucosyllactose have used recombinant *E. coli*. However, *E. coli* cells are limitedly used due to a phenomenon called "lactose killing" in which *E. coli* cells may be killed under lactose-restricted culture by lactose permease.

The present inventors suggested a method of preparing 2'-FL using recombinant *Corynebacterium glutamicum* in previous U.S. Pat. No. 10,173,1263 (registration date: 2017, Apr. 24) and U.S. Pat. No. 10,201,4925 (registration date: 2019, Aug. 21).

However, the present inventors have made various experimental attempts to find a method for economically increasing the productivity of 2'-fucosyllactose without feeding an additional medium, and developed a method of improving the productivity of final 2'-fucosyllactose by treatment with a lactase in the stationary phase or in the death phase of culture (preferably transition from the stationary phase to the death phase).

Figure 1:
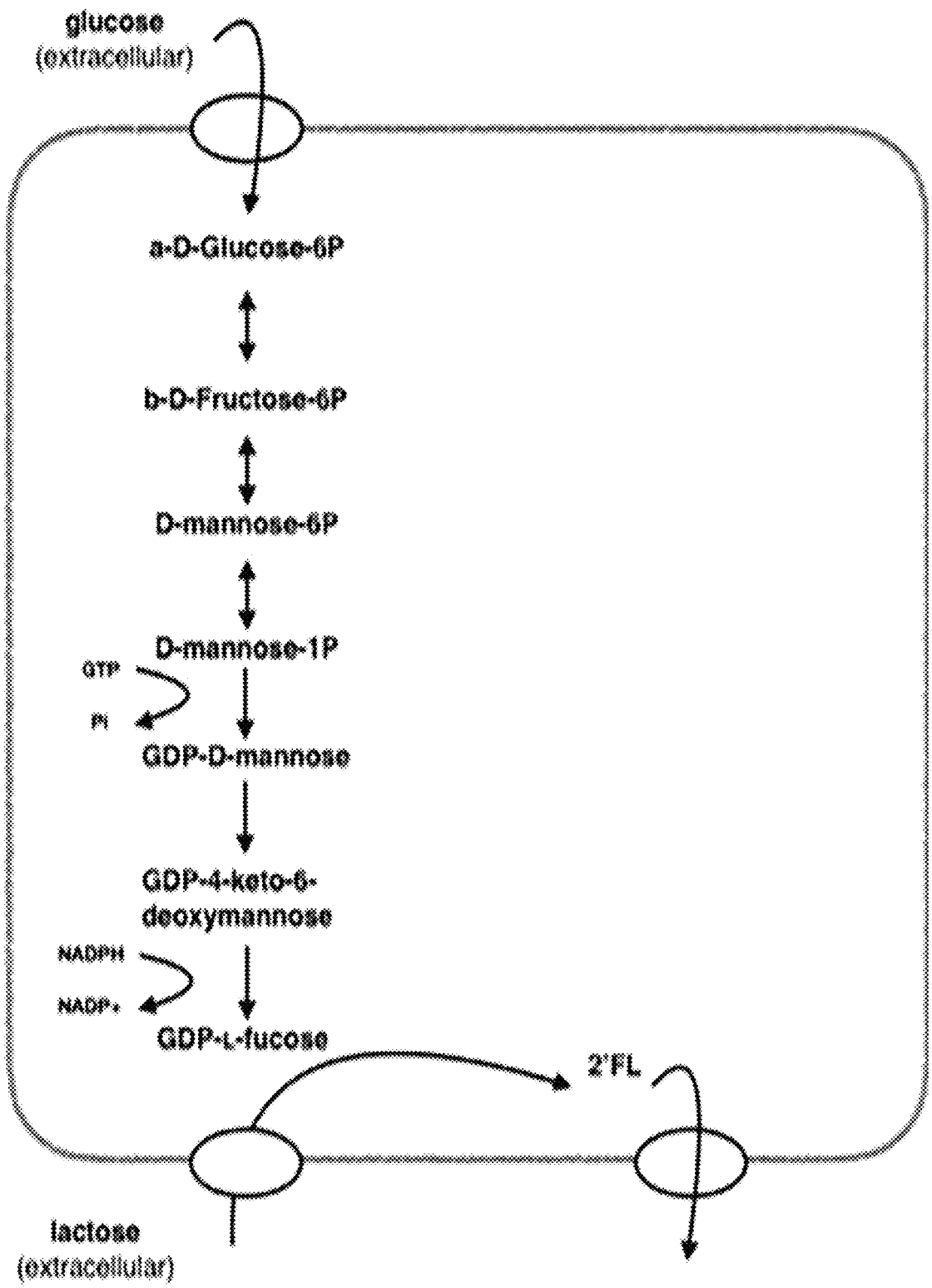
FIG. 1 is a schematic diagram illustrating a process of preparing 2'-fucosyllactose using a recombinant *Corynebacterium* strain.

Therefore, in one aspect, the present invention is directed to a method for preparing 2'-fucosyllactose by culturing recombinant *Corynebacterium glutamicum* in a medium supplemented with lactose, wherein the recombinant *Corynebacterium glutamicum* is transformed to express α-1,2-fucosyltransferase, is transformed to express GDP-D-mannose-4,6-dehydratase, is transformed to express GDP-L-fucose synthase, and is transformed to express lactose permease, and the *Corynebacterium glutamicum* has phosphomannomutase and GTP-mannose-1-phosphate guanylyltransferase, wherein a lactase is fed to the medium in a stationary phase or death phase. The process for preparing 2'-fucosyllactose using the strain of the present invention is shown in FIG. 1.

Meanwhile, in the present invention, the lactase is preferably beta-galactosidase. More preferably, the lactase is treated in an amount of 60 to 100 units per gram of lactose left in the culture medium. Lactose is degraded by lactase to produce galactose and glucose. GDP-L-fucose, which is the final substrate for the synthesis of 2'-fucosyllactose, is produced from the produced glucose, and then reacted with remaining undigested lactose to further produce 2'-fucosyllactose. Through this process, the yield of 2'-fucosyllactose can be increased by making the most of lactose, which remains as a by-product in the late stage of fermentation. In addition, another effect of reducing the burden of separating lactose in the process of separating and purifying 2'-fucosyllactose is also obtained.

Meanwhile, in the method of preparing 2'-fucosyllactose according to the present invention, the recombinant *Corynebacterium glutamicum* is preferably transformed to overexpress phosphomannomutase, and is transformed to overexpress GTP-mannose-1-phosphate guanylyltransferase. Since *Corynebacterium glutamicum* has its own genes encoding phosphomannomutase (ManB) and GTP-mannose-1-phosphate guanylyltransferase (ManC), and thus can express the same, it is not necessary to incorporate the genes encoding these enzymes, but it is necessary to overexpress the enzymes for mass production. Therefore, in the present invention, preferably, it is necessary to transform *Corynebacterium glutamicum* to overexpress the two enzymes.

Meanwhile, the term "expression" as used herein means incorporation and expression of external genes into strains in order to intentionally express enzymes that cannot be inherently expressed by the *Corynebacterium glutamicum* strain according to the present invention, and the term "overexpression" as used herein means overexpression that is induced by artificially increasing the amount of expressed enzyme in order to increase expression for mass-production, although the *Corynebacterium glutamicum* strain according to the present invention has genes encoding the corresponding enzyme and therefore can self-express the same.

Meanwhile, regarding the method for producing 2'-fucosyllactose according to the present invention, the medium preferably further includes glucose. By adding an additional ingredient to the medium, the growth of strains can be facilitated and 2'-fucosyllactose can thus be produced at higher productivity. In addition, for this purpose, when glucose or lactose is continuously fed through fed-batch culture, the growth of the cells can be further increased, and 2'-fucosyllactose can be produced with high purity, high yield, and high productivity. The detailed technologies associated with fed-batch culture are well-known in the art and are not described herein.

Meanwhile, in the method of preparing 2'-fucosyllactose of the present invention, the lactase is preferably fed to the medium at the time of transition from the stationary phase to the death phase.

Meanwhile, the following experiment showed that, according to the present invention, when treating with beta-galactosidase, which is a lactose-degrading enzyme, in the latter half of the culture stationary phase, the yield of 2'-fucosyllactose can be finally increased to 126% as compared to before enzymatic treatment. This is because 2'-fucosyllactose can be produced by producing guanosine diphosphate-L-fucose, which is the final substrate for the synthetic reaction of 2'-fucosyllactose, from glucose obtained by degradation of lactose and then reacting the guanosine diphosphate-L-fucose with undigested lactose, although guanosine diphosphate-L-fucose is not produced from glucose because no additional medium is fed. The 2'-fucosyllactose finally produced thereby is economically beneficial because it does not require additional glucose. The amount of lactose present as a by-product can be minimized while increasing the productivity of 2'-fucosyllactose using only the remaining lactose. As such, it is possible to provide a method for increasing the productivity of 2'-fucosyllactose in a safe and economically efficient manner.

Hereinafter, the present invention will be described in more detail with reference to the following examples, but the scope of the present invention is not limited to the examples, and includes variations and technical concepts equivalent thereto.

Preparation Example 1: Preparation of Recombinant Plasmids

*Escherichia* coli K-12 MG1655 and *Corynebacterium glutamicum* ATCC 13032 were used in order to produce plasmids and 2'-fucosyllactose (2'-FL), respectively.

In order to establish pFGW(Ps) plasmids, gmd-wcaG gene clusters were amplified through PCR reaction using two DNA primers, namely GW-F and GW-R, from the genomic DNAs of K-12 MG1655, *E. Coli*, the promoters of the Sod gene were amplified through PCR reaction using two DNA primers, namely Sod-F and Sod-R from the genomic DNA of *Corynebacterium glutamicum* ATCC 13032, and then pSod-Gmd-WcaG DNA fragments were synthesized through an overlapping PCR reaction using two DNA primers, namely Sod-F and GW-R.

In addition, the transcription termination sequence was amplified from the pXMJ19 plasmids through PCR reaction using two DNA primers, namely Ter-F and Ter-R, and a pSod-Gmd-WcaG-ter sequence was synthesized from the synthesized pSod-Gmd-WcaG and transcription termination sequence as templates through PCR reaction using DNA primers Sod-F and Ter-R, and was then inserted into the pCES208 plasmids sieved by the restriction enzyme, BamHI, to establish pGW plasmids.

In addition, a Tuf gene promoter was amplified through PCR reaction using two DNA primers Tuf-F1 and Tuf-R1 from the genomic DNAs of *Corynebacterium glutamicum* ATCC 13032, and α-1,2-fucosyltransferase was amplified through PCR reaction using two DNA primers, FT(Ps)-F and FT(Ps)-R, from the synthesized α-1,2-fucosyltransferase derived from *Pseudopedobacter saltans* DSM 12145, and pTuf-FT (Ps) DNA fragments were synthesized through an overlapping PCR reaction using two primers Tuf-F and FT(Ps)-R. The pTuf-FT (Ps) DNA fragments were inserted into the established pGW plasmid by treating with restriction enzyme NotI to establish PFGW(Ps) plasmids.

Meanwhile, in order to establish pXIL plasmids, lacY genes were amplified through PCR reaction using two DNA primers, namely ilvC-lacY-F and lacY pX-R, from the genomic DNAs of K-12 MG1655, *E. Coli*, the promoters of the ilvC genes were amplified through PCR reaction using two DNA primers, namely pX-ilvC-F and ilvC-lacY-R, from the genomic DNA of *Corynebacterium glutamicum* ATCC 13032, pilvC-lacY DNA fragments were synthesized through an overlapping PCR reaction using two DNA primers, namely pX-ilvC-F and ilvC-lacY-R, and the pilvC-lacY fragments were inserted into the pX plasmid (pXMJ19) treated with restriction enzymes, Not I and EcoR I to establish pXIL plasmids.

The strains, primers, plasmids, and nucleic acid and amino acid sequences used in this Preparation Example are shown in Tables 1 to 4 below.

TABLE 1

| Strains | |
|---|---|
| *E.Coli* K-12 MG1655 | F−, lambda−, rph-1 |
| *C. glutamicum* | Wild-type strain, ATCC13032 |

TABLE 2

| Nucleic acid and amino acid sequences | |
|---|---|
| gmd Nucleic acid sequence | SEQ ID NO: 1 |
| wcaG Nucleic acid sequence | SEQ ID NO: 2 |
| lacY Nucleic acid sequence | SEQ ID NO: 3 |
| FT(Ps) Nucleic acid sequence | SEQ ID NO: 4 |
| FT(Ps) Amino acid sequence | SEQ ID NO: 5 |

TABLE 3

| Primers | |
|---|---|
| Primers | Sequence (5'→3') |
| pX-ilvC-F | GTCATATGATGGTCGCGGATCCGAATTCCCAGGCAAGCTCCGC |
| ilvC-lacY-R | GTTTTTTAAATAGTACATAATCTCGCCTTTCGTAAAAATTTTGGT |
| ilvC-lacY-F | TTACGAAAGGCGAGATTATGTACTATTTAAAAAACACAAACTTTTGGATGTTCGG |
| lacY pX-R | GCCTTTCGTTTTATTTGCTCGAGTGCGGCCGCTTAAGCGACTTCATTCACCTGACGAC |
| Tuf-F1 | TGGAGCTCCACCGCGGTGGCTGGCCGTTACCCTGCGAA |
| Tuf-R1 | CAAATATCATTGTATGTCCTCCTGGACTTCG |
| FT (ps)-F | AGGACATACAATGATATTTGTAACCGGATATG |
| FT (ps)-R | CGCTTCACTAGTTCTAGAGCTTAAATAATGTGTCGAAACAGATTC |
| Sod-F | TTGGAGCTCCACCGCGGTGGCGGCCGCTCTAGAACTAGTGAAGCGCCTCATCAGCG |
| Sod-R | TACACCGGTGATGAGAGCGACTTTTGACATGGTAAAAATCCTTTCGTAGGTTTCCGCAC |
| GW-F | ATGTCAAAAGTCGCTCTCATCACCGGTGTA |
| GW-R | CAAGCTGAATTCTTACCCCGAAAGCGGTC |
| ter-F | GACCGCTTTCGGGGGTAAGAATTCAGCTTG |
| ter-R | GGTATCGATAAGCTTGATATCGAATTCCTGCAGCCCGGGGAAAAGGCCATCCGTCAGGAT |

TABLE 4

| Plasmids | | |
|---|---|---|
| Plasmid | Related features | Ref. |
| pCES208 | Km$^R$, *C. glutamicum*/*E. coli* shuttle vector | J. Microbiol. Biotechnol. (2008), 18(4), 639647 |
| pXMJ19 | Cm$^R$, *C. glutamicum*/*E. coli* shuttle vector | Biotechnology Techniques (1999), 13,437441 |
| pGW | pCES208 + Sod-gmd-wcaG | Pat. No. 10-2014925 |
| pFGW(Ps) | pCES208 + Tuf-FT(Ps) + Sod-gmd-wcaG | Pat. No. 10-2014925 |
| pXIL | pXMJ19 + ilvC-lacY | Pat. No. 10-2014925 |

Example 1: Productivity of 2'-Fucosyllactose by Lactase Treatment

This example is directed to an experiment on a method for producing 2'-fucosyllactose without an additional medium by degrading lactose, which is a substrate, by treatment with beta-galactosidase as an enzyme.

Figure 2:
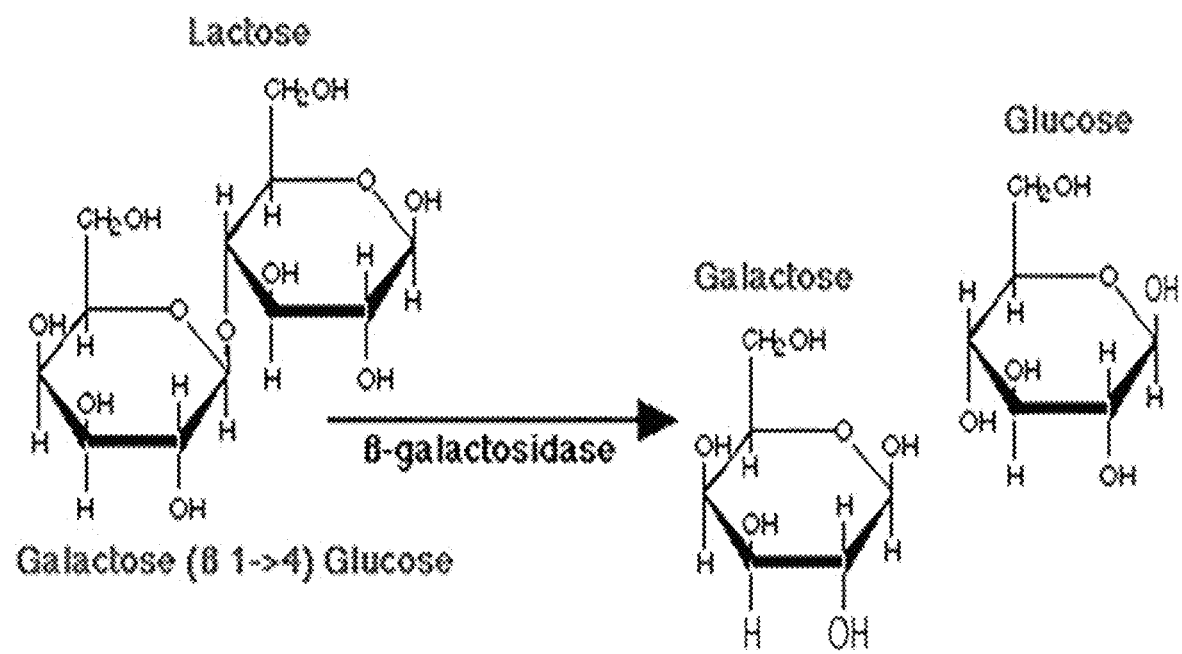
FIG. 2 is a schematic diagram illustrating the degradation of lactose using beta-galactosidase.

Conditions for culture were as follows.
Seed medium: 10 g/L yeast extract, 20 g/L casein peptone, 10 g/L sodium chloride, 5 g/L glucose
Main medium: 30 g/L yeast extract, 5 g/L ammonium sulfate, 1 g/L potassium phosphate, 1 g/L potassium phosphate, 40 g/L glucose, 20 g/L lactose
Additional medium: 15 g/L ammonium sulfate, 600 g/L glucose, 100 g/L Lactose
Enzyme: beta-galactosidase
Culture conditions: pH 7.0, 800 rpm, 25° C., Air 2VVM In the second half of the stationary phase, the feed of the additional medium was terminated and the amount of the remaining lactose was measured and treated with the enzyme beta-galactosidase in an amount of 80 units per gram of the lactose. As can be seen from FIG. 2, when lactose is degraded by the enzyme beta-galactosidase, glucose and galactose are produced.

Figure 3:
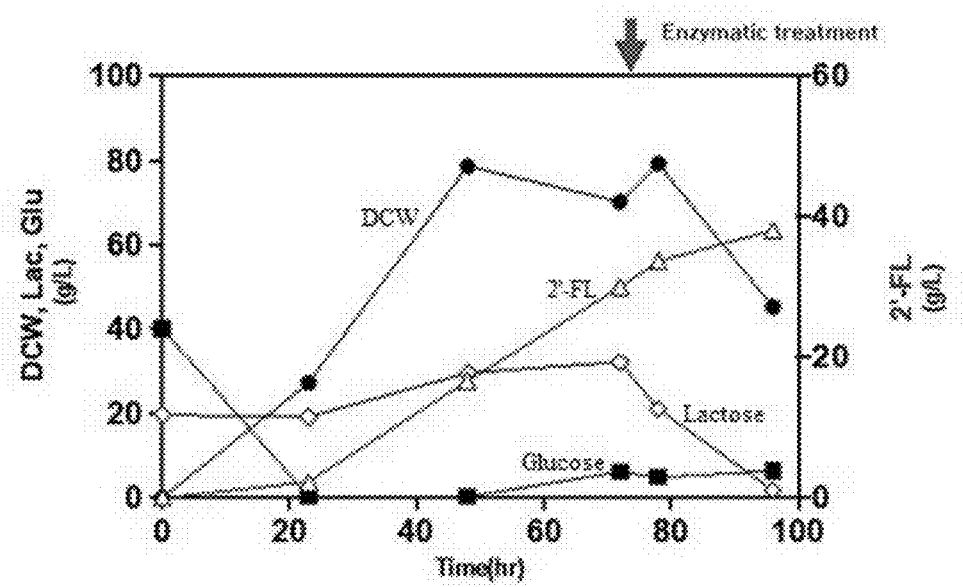
FIG. 3 is a graph showing the productivity of 2'-fucosyllactose through lactose degradation.

As a result, as can be seen from FIG. 3, 30.1 g/L of 2'-fucosyllactose is produced before enzymatic treatment without feeding an additional medium and 38.1 g/L of 2'-fucosyllactose is finally produced through lactose decomposition by an enzyme, although guanosine diphosphate-L-fucose is not produced from glucose because no additional medium is fed. Since the finally produced 2'-fucosyllactose does not require additional glucose, it is economically beneficial and 126% of 2'-fucosyllactose can be obtained using only the remaining lactose.

This result shows that GDP-L-fucose, which is a final substrate for the synthesis of 2'-fucosyllactose, is produced from glucose obtained by lactose degradation, and then is reacted with undigested lactose to produce 2'-fucosyllactose. In addition, since 2'-fucosyllactose can be further produced by maximally utilizing lactose through treatment with lactase, the culture can be terminated while minimizing the amount of lactose present as a by-product.

The invention claimed is:

1. A method for preparing 2'-fucosyllactose by culturing recombinant *Corynebacterium glutamicum* in a medium supplemented with lactose,
wherein the recombinant *Corynebacterium glutamicum* is transformed to express α-1,2-fucosyltransferase, is transformed to express GDP-D-mannose-4,6-dehydratase, is transformed to express GDP-L-fucose synthase, and is transformed to express lactose permease, and the *Corynebacterium glutamicum* has phosphomannomutase and GTP-mannose-1-phosphate guanylyltransferase,
wherein beta-galactosidase is fed into the medium in a stationary phase or death phase.

2. The method according to claim 1, wherein the recombinant *Corynebacterium glutamicum* is transformed to overexpress phosphomannomutase, and is transformed to overexpress GTP-mannose-1-phosphate guanylyltransferase.

3. The method according to claim 1, wherein the medium comprises glucose.

4. The method according to claim 3, wherein the method is performed by fed-batch culture of further feeding glucose or lactose during culture.

5. The method according to claim 1, wherein the beta-galactosidase is fed to the medium at a time of transition from the stationary phase to the death phase.

* * * * *